(12) United States Patent
Versteegh

(10) Patent No.: US 9,211,438 B2
(45) Date of Patent: Dec. 15, 2015

(54) NECK MUSCLE EXERCISER AND METHOD OF ASSESSING NECK MUSCLE PERFORMANCE

(71) Applicant: Theodore Henry Versteegh, London (CA)

(72) Inventor: Theodore Henry Versteegh, London (CA)

(*) Notice: Subject to any disclaimer, the term of this patent is extended or adjusted under 35 U.S.C. 154(b) by 162 days.

(21) Appl. No.: 14/024,948

(22) Filed: Sep. 12, 2013

(65) Prior Publication Data

US 2015/0072836 A1   Mar. 12, 2015

(51) Int. Cl.
| | |
|---|---|
| *A63B 23/025* | (2006.01) |
| *A63B 21/065* | (2006.01) |
| *A63B 21/00* | (2006.01) |
| *A63B 21/06* | (2006.01) |

(52) U.S. Cl.
CPC ......... *A63B 23/025* (2013.01); *A63B 21/00065* (2013.01); *A63B 21/065* (2013.01); *A63B 21/0608* (2013.01); *A63B 21/1407* (2013.01)

(58) Field of Classification Search
CPC .. A63B 23/025; A63B 3/0406; A63B 3/0433; A63B 3/124; A63B 21/154; A63B 21/06; A63B 21/0608; A63B 21/0615; A63B 21/08; A63B 21/065; A63B 2230/00; A63B 21/072; A63B 21/0724; A63B 21/0726; A63B 21/0728; A63B 21/075; A63B 21/078; A63B 2021/0722; A42B 304/06; A61B 5/4528

USPC ............ 446/27; 472/133, 51; 600/595
See application file for complete search history.

(56) References Cited

U.S. PATENT DOCUMENTS

| | | | | | |
|---|---|---|---|---|---|
| 1,530,748 | A | * | 3/1925 | Alastalo | 482/10 |
| 2,051,366 | A | * | 8/1936 | Catron | 482/10 |
| 2,958,156 | A | * | 11/1960 | Schmahl et al. | 446/27 |
| 3,184,884 | A | * | 5/1965 | Petrucelli | 446/27 |
| 4,168,060 | A | * | 9/1979 | Hohenfeldt | 482/10 |
| 4,339,124 | A | * | 7/1982 | Vogler | 482/10 |
| 6,000,066 | A | * | 12/1999 | Williams | 2/422 |

* cited by examiner

*Primary Examiner* — Oren Ginsberg
*Assistant Examiner* — Megan Anderson
(74) *Attorney, Agent, or Firm* — Brunet & Co. Ltd.; Robert A. H. Brunet

(57) ABSTRACT

Training neck muscles in such a way as to improve responsiveness to head acceleration forces, and to help prevent concussion and/or screen subjects who are at high risk of concussion, especially from contact sports, the neck muscles may be trained to improve strength and responsiveness to head acceleration. This may be accomplished by a device and/or method of training that incorporates an adjustable centripetal force about a fixed axis on the head. The centripetal force may be adjusted through varying the weight and/or length of a force arm. Neck muscle performance may be measured by the number of revolutions of the force arm completed over a pre-determined time period or the time required to complete a pre-determined number of revolutions of the force arm.

21 Claims, 3 Drawing Sheets

NECK MUSCLE EXERCISER AND METHOD OF ASSESSING NECK MUSCLE PERFORMANCE

FIELD

This application relates to physical training devices and to methods for assessing muscle performance, in particular to such devices and methods related to neck muscles.

BACKGROUND

There are potentially very serious and lifelong consequences to suffering a concussion or other head injury. This concern is not just for professional athletes; it holds true for anyone involved in high risk sports as well as military personnel. Concussions are complex pathophysiological processes affecting the brain, induced by traumatic biomechanical forces. Research is starting to show the important role that neck muscles play in absorbing concussion forces from head impact. Recent research shows that for every pound of increased neck strength, concussion risk decreases by 5%. Previous research has also demonstrated how head peak acceleration and HIT scores, a proxy for concussion, can be drastically reduced in biomechanical models by increasing neck stiffness. What the sporting world lacks is an effective method of harnessing this natural shock absorption system and enhancing it.

Methods of strength training the neck currently exist, and these methods may increase neck girth. However to help the neck muscles protect the brain the reflexes and responsiveness of these muscles' should also be improved. As is known, a tense muscle provides much more resistance to acceleration than does a limp muscle.

There exists a need in the art for devices and methods that safely strengthen the neck muscles, increase neck girth and stiffness and/or improve the neck's reflex response enhancing protection further. There also remains a need for devices and methods that can be used to evaluate a subject's pre-participation concussion risk by assessing performance and accurately predicting subjects most at risk.

SUMMARY

To help prevent concussion and/or screen subjects who are at high risk of concussion, especially from contact sports, the neck muscles may be trained to improve strength and responsiveness. This may be accomplished by a device and/or method of training that incorporates an adjustable centripetal force about a fixed axis on the head. A magnitude of the centripetal force may be adjusted through varying the weight and/or length of a force arm. Neck muscle performance may be measured by the number of revolutions of the force arm completed over a pre-determined time period or the amount of time required to complete a pre-determined number of revolutions of the force arm. Thus, neuromuscular and strength training of the neck muscles, as well as neck muscle performance measurement, may be accomplished by using centripetal force to generate resistance.

In one aspect, there is provided a neck muscle exercising or performance assessment device comprising: a substantially rigid elongated element configured to be length adjustable and/or to demountably receive one or more demountable weights selectively positionable along a length of the elongated element; a mount on which the elongated element is rotatably mounted proximate a first end of the elongated element, the elongated element rotatable around a central axis, the elongated element extending radially from the central axis; and, headwear to which the mount is rigidly attached, the headwear wearable on a subject's head so that the central axis is through the subject's head and rotational motion of the subject's head causes the elongated element to revolve around the central axis.

In another aspect, there is provided a method of assessing neck muscle performance of a test subject, comprising: obtaining a neck muscle performance score of a test subject by determining a number of revolutions in a pre-determined period of time of a radially extending substantially rigid elongated element revolving around a central axis through a head of the test subject, or determining an amount of time required for a pre-determined number of revolutions of a radially extending substantially rigid elongated element revolving around a central axis through a head of the test subject, the revolutions of the elongated element being caused by action of neck muscles of the test subject; and, comparing the neck muscle performance score to a standard neck muscle performance score to assess the neck muscle performance of the test subject in relation to the standard.

Adjusting the magnitude of the centripetal force acting on the elongated element may be accomplished by adjusting length of the elongated element, adjusting position of one or more demountable weights on the elongated element, adding or removing weights from the elongated element or any combination thereof. In this way, resistance may be adjusted up or down to requiring greater or lesser effort by the subject to effect revolution of the elongated element around the central axis. The elongated element has a first end proximate the mount and second end remote from the mount. Longer elongated elements, larger weights and weights positioned nearer the second end provide greater moments of inertia and larger centripetal forces.

The elongated element may comprise, for example, a rod, tube or the like. Length adjustment of the elongated element may be accomplished in a number of ways, for example as follows: The elongated element may comprise telescoping members in which at least one member is housed within and slidable longitudinally in another hollow member. A locking mechanism, for example a spring-loaded pin in a pin receiving aperture may be used to lock the telescoping members together to prevent the members from sliding in or out during operation of the device. The elongated element may comprise members that are connectable longitudinally (end to end), for example with mated ends of a push-in type or a male/female thread type. Locking mechanisms may also be used to prevent the members from separating under use. The elongated element may comprise overlapping members, for example flat plates secured together by fasteners, e.g. nuts and bolts, at points along the length. The elongated element may be dismounted from the mount and replaced by an elongated element of different length.

A demountable weight may be mounted on and positioned on the elongated element in a number of ways, for example as follows: The weight may be clamped on to the elongated element at a desired position. The weight may comprise a through aperture through which the elongated element may be inserted and then secured at a desired position on the length of the elongated member. In one aspect, the elongated element is threaded with screw threads along at least a portion of the length for receiving one or more matingly threaded nuts to secure the demountable weight at one or more selected positions along the length of the elongated element. The threaded nuts themselves may be viewed as demountable weights. Alternatively or additionally, in another aspect, the demountable weight may comprise a threaded through aperture, the weight being selectively positionable along the length of the elongated element by screwing the weight onto the elongated element until a desired position is attained. The threaded weights may be viewed as large threaded nuts. In one aspect, the elongated element comprises a rod for receiving the one or more demountable weights at the second end, and the first end of the rod is bent at an angle from the second end, the first end rotatably mounted on the mount. In a particularly preferred aspect, the demountable weight may be secured to the elongated elements with one or more pins, clip or the like.

Rotatably mounting the elongated element on the mount may be accomplished in a number of ways, for example with a rotation bearing in a bearing block, a ball and socket joint or a pin in receiver joint. The elongated element revolves around a central axis and extends radially from the central axis. Preferably, the radius formed by the elongated element is perpendicular to the central axis.

In use, the subject wears the device on the head. For comfort, security and ease of operation, the mount for the elongated element is rigidly attached to the headwear. The headwear may be rigid (e.g. a plastic helmet) or semi-rigid (e.g. an array of adjustable nylon straps) device with cushioning on the underside that is in contact with the wearer's head that is able to transmit tension generated from the neck muscles up through to the rotatable mount. The mounting of the rotatable mount to the headwear may be accomplished in a variety of methods. For example, the rotatable mount may be molded to conform to the shape of a snugly fitting helmet and then held in place by bolts and nuts, straps, clips, cables, bands or some other fastening array. The helmet would then have a snugly fitting chin strap with two or more anchors to the helmet (for example in line with the temple bone and mastoid process of the skull on the helmet) to secure the device to the wearer's head and to transmit the rotation force from the neck muscles up through the device.

Preferably, the mount is rigidly attached to the headwear at a top of the subject's head and the elongated element revolves around the central axis above the subject's head in a plane perpendicular to the central axis running through the top of the subject's head down through the subject's torso. In use, rotation of the subject's head causes the longitudinal element to revolve around the central axis by virtue of the rotatable mounting. Such rotation of the head is due to the subject's neck muscles, which are exercised by the rotating motion. Thus, the subject uses the muscles of the neck to generate and maintain an orbital motion of the elongated element around the central axis. The elongated element may be free to revolve through a complete 360° circle and continue to revolve through an unlimited number of circles. The headwear may comprise a plurality of locations to which the mount may be rigidly attached providing different exercise options for the subject's neck muscles as the elongated element would describe circles around a different central axis and/or in a different plane than when the mount is at the top of the head. Therefore, while the mount is rigidly attached to the headwear, the mount may be dismountable from and remountable to the headwear. In one aspect, the headwear may comprise a helmet. For safety and ease of use, the headwear should fit the subject snugly and may comprise a securement element for securing the headwear to the head of the subject, for example a chin strap.

The device may comprise a counter for counting a number of revolutions of the elongated element during use. The counter may comprise, for example, a position sensor, e.g. a camera, an accelerometer, an inclinometer, an RFID tag, a magnet, etc., and may be in communication with a recorder, for example a digital data processor and/or storage medium (e.g. a bicycle speedometer type counter, a computer, hard drive, flash drive, optical disc, etc.), containing software for counting the number of revolutions. The counter is preferably mounted on the elongated element.

Assessing neck muscle performance of the subject may be achieved by one or more of: Varying the weight on the elongated element, the time required to perform a pre-determined number of revolutions or the number of revolutions performed during a pre-determined amount of time. This information may then be used to evaluate the neck muscle performance (e.g. strength and/or neuromuscular capabilities) of the subject. This information may be compared to a group of average and/or standardized values to determine the subject's risk of concussion, whiplash or other injury. This information may also be used to screen for participation in some sports or activities as well as assess for improvement of neuromuscular strength function.

The present device is portable and can be used in a variety of different settings, for example clinics, playing fields or arenas, and research facilities. Further, the ability to readily adjust the centripetal force experienced by the subject provides flexibility of operation and useability with different subjects having different neck muscle capabilities, and permits assessment of neck muscle performance. The device is useful for training the neck to improve its ability to respond to acceleration forces and protect the head and neck from injury (e.g. concussion or whiplash), rehabilitating weak or injured neck muscles, neuromuscular training and rehabilitation for neck proprioception and coordination, screening for neck strength and function for assessment of concussion risk, screening for neck strength and function for whiplash risk, rehabilitating subjects who have suffered from whiplash or concussion and training for balance.

Further features will be described or will become apparent in the course of the following detailed description.

BRIEF DESCRIPTION OF THE DRAWINGS

For clearer understanding, preferred embodiments will now be described in detail by way of example, with reference to the accompanying drawings, in which.

DETAILED DESCRIPTION

Figure 1:
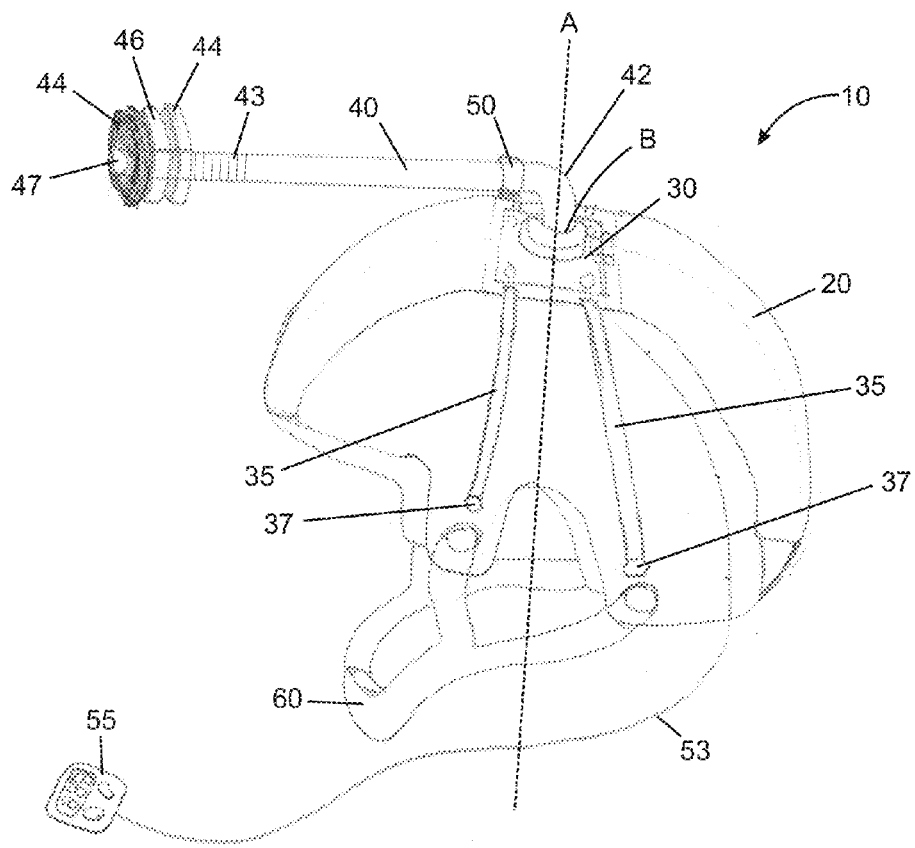
FIG. 1 is a perspective view of a neck muscle exercising or performance assessment device.
Figure 2:
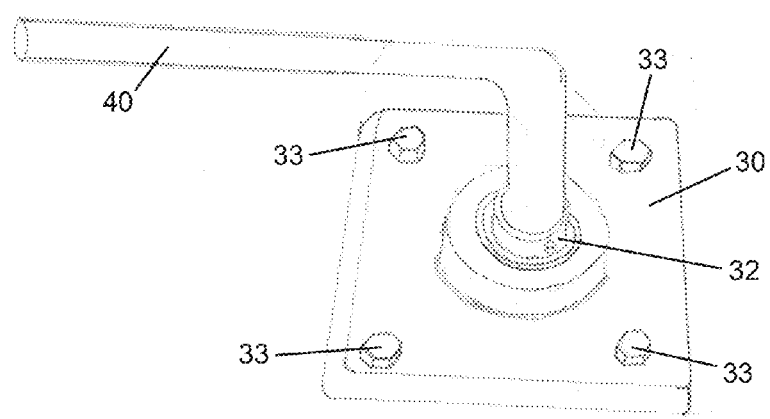
FIG. 2 depicts a bearing flange shown in FIG. 1 with a rod rotatably mounted thereon.

Referring to FIG. 1 and FIG. 2, a neck muscle exercising or performance assessment device 10 comprises a helmet 20 to the top of which a bearing flange 30 is fixedly attached by cables 35 secured to rivets 37 in the helmet 20. Rotatably mounted on the bearing flange 30 is a rod 40 extending radially outward from an axis A through the point of rotation B where one end of the rod 40 is rotatably secured in a rotational bearing secured in the bearing flange 30. The rod 40 has a 90° bend 42 proximate the end secured at point of rotation B so that the rod 40 may revolve around the axis A while pointing radially outward form the axis A. The rod 40 is threaded along part of its length with screw threads 43 for matingly receiving nuts 44 that secure demountable weight 46 near a far end 47 of the rod 40. There is one nut 44 on each side of the weight 46, the weight 46 comprising a central aperture through which the rod 40 is inserted. The device 10 further comprises a counter including a magnet 50 from a bicycle speedometer mounted on the rod 40 in communication through wire 53 with a bicycle speedometer 55 for counting the number of full revolutions of the rod 40 around the axis A. A chin strap 60 securely holds the helmet 20 on the head of a subject. FIG. 2 depicts a magnified view of the rod 40 rotatably mounted on the bearing flange 30 by a rotational bearing 32 in the bearing flange 30. The bearing flange 30 comprises securement bolts 33 for securing the cables 35 to the bearing flange 30.

Figure 3A:
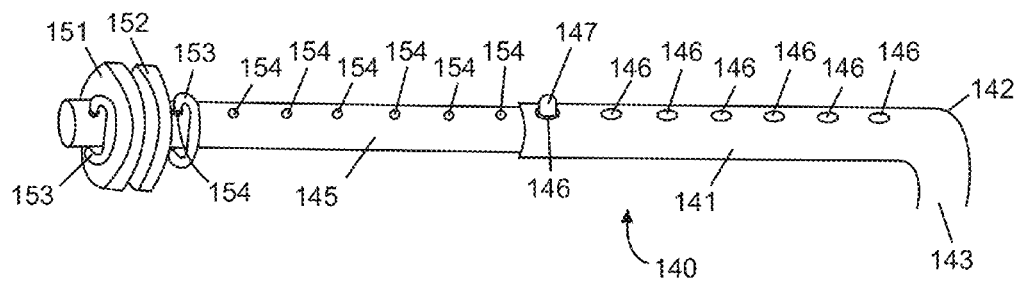
FIG. 3A depicts a telescoping rod in a fully extended configuration having a plurality of weights proximate a distal end.
Figure 3B:
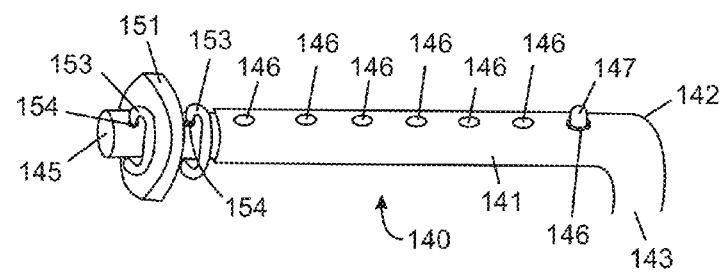
FIG. 3B depicts the telescoping rod of FIG. 3A in a fully retracted configuration and having a single weight proximate the distal end.
Figure 3C:
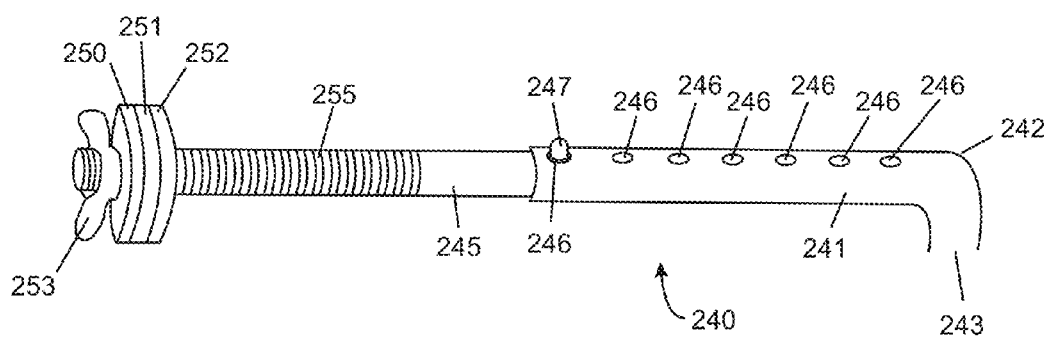
FIG. 3C depicts a telescoping rod in a fully extended configuration having a plurality of weights proximate a distal end secured by a wing nut on a threaded portion of the rod.

In use, a subject puts on the helmet 20 and secures the chin strap 60 under his chin in the same manner as donning any helmet of similar nature. By rotating his head clockwise or counter-clockwise in a rhythmic and orbital fashion, the subject can induce the rod 40 to begin revolving around the axis A by virtue of being rotatably mounted on the bearing flange 30. The weight 46 being located proximate the far end 47 of the rod 40 provides a heightened moment of inertia and increases centripetal force on the rod 40, which provides increased resistance to neck muscles of the subject. The increased resistance exercises the neck muscles more vigorously. More or less resistance may be provided by adding more weight or adjusting the length of the rod, some variations of which are shown in FIGS. 3A-C. The subject may follow a prescribed regimen and the counter may be used to ensure that the subject accurately follow the regimen.

The device may be used for exercise only or for performance assessment. In one aspect, the device may be used to assess the risk of concussion. Risk of concussion may be assessed and determined by correlating a subject's ability to perform on the device i.e. time needed to complete a pre-determined number of revolutions on the device at a specified weight and rotatable arm length and concussion risk. The more time a subject requires to perform the pre-determined number of revolutions, the weaker and less responsive his/her neck may be and therefore the more prone he/she may be to concussion. As an example, when assessing the performance of a team of hockey players on the device and then following this team during a hockey season, those who perform more poorly on the device may have an increased likelihood of suffering a concussion. If this is the case then it is likely that a certain performance level will be associated with the natural baseline risk for suffering a concussion and that performance levels below this line will be at higher risk for concussion. It may therefore be possible to screen players of nearly any sport to determine those that are at a high and or higher risk of concussion. In the event of an injury, a player who has suffered a concussion or whiplash may have a drop in performance on the device as the muscles of the neck are commonly injured during a concussion, and always during whiplash. Therefore, the device can be used to assess when a player is ready to return to sport after suffering a concussion by delaying return to sport until the player is able to perform on the device to the previously described baseline.

FIGS. 3A-3B depict a telescoping rod 140 comprising an outer rod 141 having a 90° elbow 142 and an inner rod 145 that may telescope within the outer rod 141. The outer rod 141 is rotatably mounted to a bearing flange (not shown) at a proximal end 143. The outer rod 141 comprises a series of apertures 146 arranged along a length of the outer rod 141 for receiving a spring-loaded pin 147 situated near a proximal end of the inner rod 145. The spring-loaded pin 147 may be engaged in any one of the apertures 146 to adjust the overall length of the rod 140. To adjust the length of the rod 140, the spring-loaded pin 147 is depressed to disengage the pin 147 from an aperture 146 and the inner rod 145 is slid proximally or distally within the outer rod 141 until the spring-loaded pin 147 engages the next aperture 146. The outer rod 141 may comprise any number of apertures 146, and each aperture represents a length setting for the rod 140. The telescoping rod 140 may be of any desired length, for example 12 inches in the fully extended configuration (FIG. 3A) and 6 inches in the fully retracted configuration (FIG. 3B). Weights, for example two weights 151, 152 as seen in FIG. 3A or one weight 151 as seen in FIG. 3B, may be mounted on the inner rod 145. To secure the weights 151, 152 on the inner rod 145, securement clips 153 may mounted on the inner rod 145, the clips 153 having ends that may be inserted through clip apertures 154 on the inner rod 145. Two clips 153 may be used on each side of the weight or weights (e.g. weights 151, 152 as seen in FIG. 3A, or weight 151 as seen in FIG. 3B). Only one clip distally of the weight may be needed if the inner rod is retracted sufficiently that the outer rod helps secure the weight or weights in place proximally. The inner rod 145 may comprise a series of any number of clip apertures 154, and may comprise an opposed series of clip apertures, the opposed clip aperture receiving opposite ends of the securement clips 153. A series of clip apertures 154 permits mounting the weights 151, 152 at a variety of positions along the inner rod 145 in order to change the moment of inertia for the device on which the rod 140 is mounted.

FIG. 3C depicts a second embodiment of a telescoping rod 240 comprising an outer rod 241 having a 90° elbow 242 and an inner rod 245 that may telescope within the outer rod 241. The outer rod 241 is rotatably mounted to a bearing flange (not shown) at a proximal end 243. The telescoping rod 240 comprises a spring-loaded pin 247 near a proximal end of the inner rod 245, and apertures 246 in the outer rod 241 to engage the spring-loaded pin 247 in a manner similar to that of the telescoping rod 140 described in relation to FIGS. 3A-B. However, instead of the inner rod 245 possessing clip apertures, at least a portion of the inner rod 245 comprises screw threads 255 onto which weights 250, 251, 252 may be threaded. The weights may be secured at any position along the threaded portion 255 by nuts, for example a wing nut 253 distal of the weights 250, 251, 252, and if desired, another nut on the proximal side of the weights 250, 251, 252. The weights 250, 251, 252 may be threaded to any desired location along the threaded portion 255 to change the moment of inertia of the device.

Figure 4A:
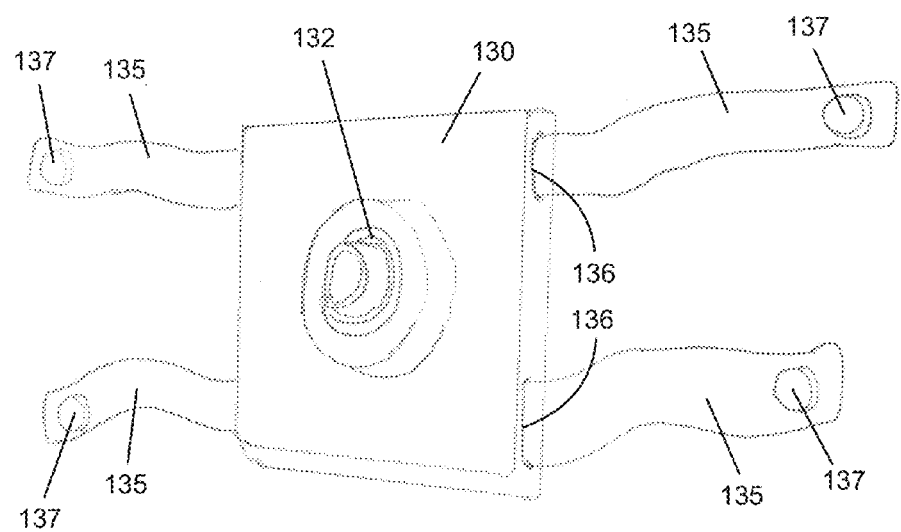
FIG. 4A depicts one embodiment of an attachment mechanism for mounting a bearing flange on headwear; and, FIG. 4B depicts another embodiment of an attachment mechanism for mounting a bearing flange on headwear.
Figure 4B:
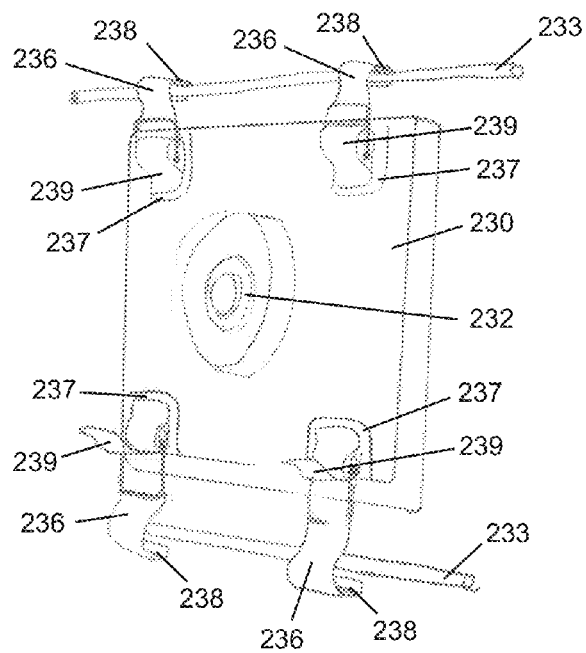

FIGS. 4A and 4B depict different embodiments of attachment mechanisms for mounting a bearing flange on headwear, for example a helmet. In FIG. 4A, a bearing flange 130 comprising a rotational bearing 132 has straps 135 mounted therein by feeding the straps 135 through through-apertures 136 in edges of the bearing flange 130. Alternatively, instead of two straps there could be four straps, each strap attached to the bearing flange. The straps may alternatively be secured to the bearing flange on an upper or lower surface of the flange rather than an edge or edges. The straps 135 may be configured so that straps or parts of straps are situated on opposed sides of the bearing flange 130 for better securement efficiency. The straps 135 may be secured to the headwear by bolts, rivets, stitching and the like at securement structures 137 on the straps 135, preferably proximate ends of the straps 135. Any number or arrangement of straps may be used to ensure proper securement of the bearing flange 130 on the headwear.

In FIG. 4B, a bearing flange 230 comprising a rotational bearing 232 has lever buckles 237 attached thereto. The lever buckles 237 comprise lever handles 239 pivotally mounted on the lever buckles 237 and operatively connected to hooks 238 through connecting straps 236. The hooks 238 are configured to engage mounting struts 233 mounted to headwear (e.g. a helmet) (not shown). The mounting struts 233 may be secured to the headwear, for example with U-bolts or clips. The mounting struts 233 are spaced apart such that when the lever handles 239 are in an "up" position, the connecting straps 236 have sufficient length for the hooks 238 to hook over the mounting struts 233, as seen in the lower part of FIG. 4B. When the lever handles 239 are in a "down" position with the hooks 238 hooked over the mounting struts 233, the connecting straps 236 are pulled toward the buckles 237 tightening the hooks 238 on the mounting struts 233, as seen in the upper part of FIG. 4B. Any number and arrangement of lever buckles may be used to ensure proper securement of the bearing flange 230 on the headwear. Mounting struts may be located anywhere on the headwear and a plurality of mounting struts on the headwear offer the opportunity for mounting the bearing flange in different locations.

Advantageously, the attachment mechanisms for mounting the bearing flange on headwear are readily removable and re-mountable to permit exchange of headwear or to move the bearing flange to a different location on the headwear.

The novel features will become apparent to those of skill in the art upon examination of the description. It should be understood, however, that the scope of the claims should not be limited by the embodiments, but should be given the broadest interpretation consistent with the wording of the claims and the specification as a whole.

The invention claimed is:

1. A neck muscle exercising or performance assessment device comprising:
   a substantially rigid elongated element configured to demountably receive one or more demountable weights selectively positionable along a length of the elongated element;
   a mount on which the elongated element is rotatably mounted proximate a first end of the elongated element, the elongated element rotatable around a central axis, the elongated element extending radially from the central axis;
   headwear to which the mount is rigidly attached, the headwear wearable on a head of a subject so that the central axis is through the head and rotational motion of the head causes the elongated element to revolve around the central axis; and,
   a counter configured to count a number of revolutions of the elongated element.

2. The device according to claim 1, wherein the elongated element is configured to receive the one or more demountable weights, and the one or more demountable weights is secured on the elongated element by one or more pins or clips.

3. The device according to claim 2, wherein the elongated element comprises telescoping members.

4. The device according to claim 1, wherein the headwear comprises a securement element for securing the headwear to the head of the subject.

5. The device according to the claim 4, wherein the headwear comprises a helmet having a chin strap.

6. The device according to claim 1, wherein the counter comprises a magnet mounted on the elongated element in communication with a bicycle speedometer.

7. The device according to claim 1, wherein the elongated element is configured to receive the one or more demountable weights and the one or more demountable weights comprise through apertures through which the elongated element is inserted.

8. The device according to claim 1, wherein the elongated element comprises screw threads along at least a portion of a length for receiving one or more matingly threaded nuts for securing the one or more demountable weights at one or more selected positions along the length of the elongated element.

9. The device according to claim 1, wherein the elongated element is configured to receive the one or more demountable weights, the one or more demountable weights comprise threaded through apertures and the elongated element comprises screw threads along at least a portion of the length for matingly receiving the threaded through apertures of the one or more demountable weights, the one or more demountable weights being selectively positionable along the length by screwing the weights onto the elongated element until a desired position is attained.

10. The device according to claim 1, wherein the elongated element comprises telescoping members.

11. The device according to claim 1, wherein the elongated element is rotatably mounted on the mount by a rotational bearing.

12. The device according to claim 1, wherein the elongated element comprises a second end for receiving the one or more demountable weights and the first end is bent at an angle from the second end, the first end rotatably mounted on the mount.

13. The device according to claim 1, wherein the mount is rigidly attached to the headwear at a top of the head and the elongated element revolves around the central axis above the head.

14. The device according to claim 1, wherein the headwear comprises a plurality of locations to which the mount may be rigidly attached.

15. The device according to claim 1, wherein the counter comprises a bicycle speedometer or accelerometer.

16. A method of assessing neck muscle performance of a test subject, comprising:
   (a) obtaining a neck muscle performance score of a test subject by
      determining a number of revolutions in a pre-determined period of time of a radially extending substantially rigid elongated element revolving around a central axis through a head of the test subject, or
      determining an amount of time required for a pre-determined number of revolutions of the radially extending substantially rigid elongated element revolving around the central axis through the head of the test subject,
      the revolutions of the elongated element being caused by action of the neck muscles of the test subject; and,
   (b) comparing the neck muscle performance score to a standard neck muscle performance score to assess the neck muscle performance of the test subject in relation to the standard.

17. The method according to claim 16, wherein the standard neck muscle performance score comprises an average of neck muscle performance scores of a plurality of subjects from a same or similar field of endeavor as the test subject.

18. The method according to claim 16, further comprising:
   (c) adding or removing weight from the elongated element, adjusting a position of the weight on the elongated element or adjusting a length of the elongated element to adjust a magnitude of a centripetal force acting on the elongated element and obtaining a second neck muscle performance score of the test subject at the adjusted centripetal force, obtaining the second neck muscle performance score accomplished as in part (a) for the same pre-determined period of time or pre-determined number of revolutions.

19. The method according claim 16 using a device comprising:

the substantially rigid elongated element configured to be demountably receive one or more demountable weights selectively positionable along a length of the elongated element;

a mount on which the elongated element is rotatably mounted proximate a first end of the elongated element, the elongated element rotatable around the central axis, the elongated element extending radially from the central axis;

headwear to which the mount is rigidly attached, the headwear wearable on the head of the subject so that the central axis is through the head and rotational motion of the head causes the elongated element to revolve around the central axis; and a counter configured to count a number of revolutions of the elongated element, to obtain the neck muscle performance score of the test subject.

20. The method according to claim 16, wherein a risk of concussion of the tests subject is determined by correlating the amount of time required for the pre-determined number of revolutions at either a specified weight on and length of the elongated element or a certain centripetal force with concussion risk as determined by average performance scores attained by a plurality of test subjects.

21. The method according to claim 16, wherein, following diagnosis of a head or neck injury in the test subject, determining whether the test subject is ready to return to normal activities for a field of endeavor of the test subject by correlating the amount of time required for the pre-determined of revolutions at either a specified weight on and length of the elongated element or a certain centripetal force with previously determined performance scores attained for the test subject prior to the diagnosis of the head or neck injury.

* * * * *